(12) United States Patent
Saffran

(10) Patent No.: US 7,171,698 B2
(45) Date of Patent: Feb. 6, 2007

(54) EARMUFF HAVING ANATOMICALLY CORRECT EAR CUPS

(75) Inventor: Michael D. Saffran, Genoa, NV (US)

(73) Assignee: Jackson Products, Inc., St. Charles, MO (US)

( * ) Notice: Subject to any disclaimer, the term of this patent is extended or adjusted under 35 U.S.C. 154(b) by 372 days.

(21) Appl. No.: 10/706,429

(22) Filed: Nov. 12, 2003

(65) Prior Publication Data

US 2004/0154082 A1  Aug. 12, 2004

Related U.S. Application Data

(60) Provisional application No. 60/445,744, filed on Feb. 7, 2003.

(51) Int. Cl.
  *A42B 1/06*  (2006.01)
(52) U.S. Cl. .............................. 2/209; 2/423; 381/71.6
(58) Field of Classification Search ............... 2/209, 2/423; 381/309, 374, 72, 71.6; 181/129
See application file for complete search history.

(56) References Cited

U.S. PATENT DOCUMENTS

| | | | |
|---|---|---|---|
| 2,782,423 A * | 2/1957 | Simon et al. .................. 2/209 | |
| 3,952,158 A | 4/1976 | Kyle et al. | |
| 4,404,434 A * | 9/1983 | Pelt et al. ................... 381/383 | |
| 4,459,707 A | 7/1984 | Stallings | |
| 4,463,223 A * | 7/1984 | Yamanoi et al. ............. 381/383 | |
| 4,465,159 A | 8/1984 | Stallings | |
| 4,471,496 A * | 9/1984 | Gardner et al. ................ 2/209 | |
| 4,574,912 A | 3/1986 | Fuss et al. | |
| 4,689,822 A * | 8/1987 | Houng ........................ 381/379 | |
| D292,400 S | 10/1987 | Boggs et al. | |
| 4,756,028 A | 7/1988 | Scanlon | |
| 4,771,454 A | 9/1988 | Wilcox, Jr. | |
| D299,337 S | 1/1989 | Wiegel | |
| 4,796,307 A | 1/1989 | Vantine | |
| 4,935,965 A | 6/1990 | Wassell | |
| 4,944,361 A | 7/1990 | Lindgren et al. | |
| D326,855 S | 6/1992 | Bose et al. | |
| 5,241,971 A | 9/1993 | Lundin | |
| 5,293,647 A * | 3/1994 | Mirmilshteyn et al. ........ 2/209 | |
| 5,384,857 A | 1/1995 | Nordin et al. | |
| D375,584 S | 11/1996 | Westerdal | |
| 5,826,582 A | 10/1998 | Sheehan et al. | |
| 5,835,609 A | 11/1998 | LeGette et al. | |
| 5,862,241 A | 1/1999 | Nelson | |
| 6,163,615 A | 12/2000 | Callahan | |
| 2004/0216946 A1* | 11/2004 | Lenhard-Backhaus ...... 181/129 | |

FOREIGN PATENT DOCUMENTS

DE  26 42 786 A1 *  6/1978

* cited by examiner

*Primary Examiner*—Gary L. Welch
*Assistant Examiner*—Richale L. Haney
(74) *Attorney, Agent, or Firm*—Dunlap Codding & Rogers, P.C.

(57) ABSTRACT

An earmuff having anatomically correct ear cups, which are axially rotatable to ensure a proper fit over a person's ears and laterally rotatable when the earmuff is disposed in a storage position around the person's neck.

13 Claims, 5 Drawing Sheets

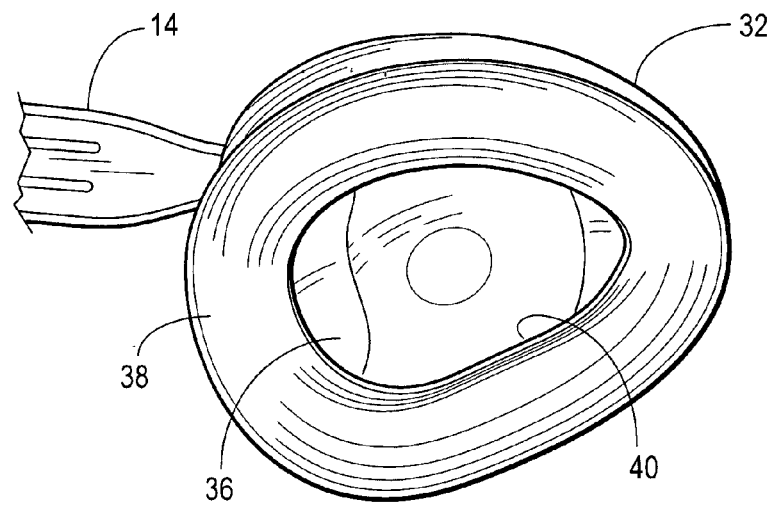
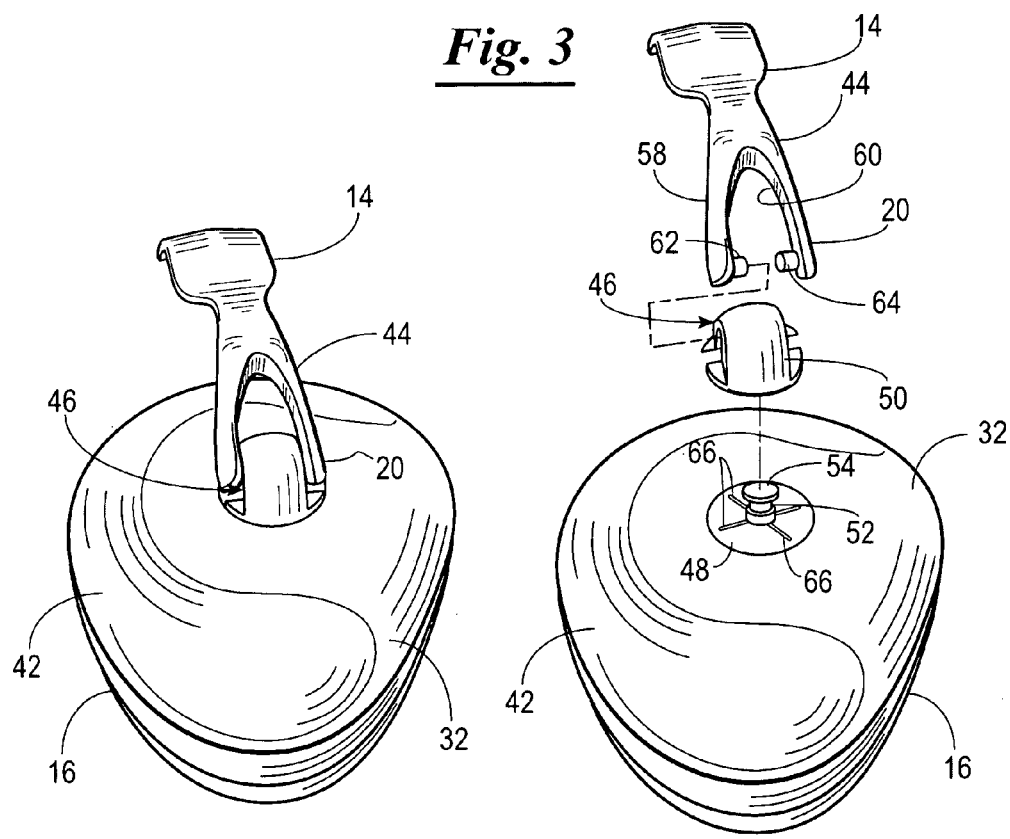
Fig. 3
Fig. 4
Fig. 5

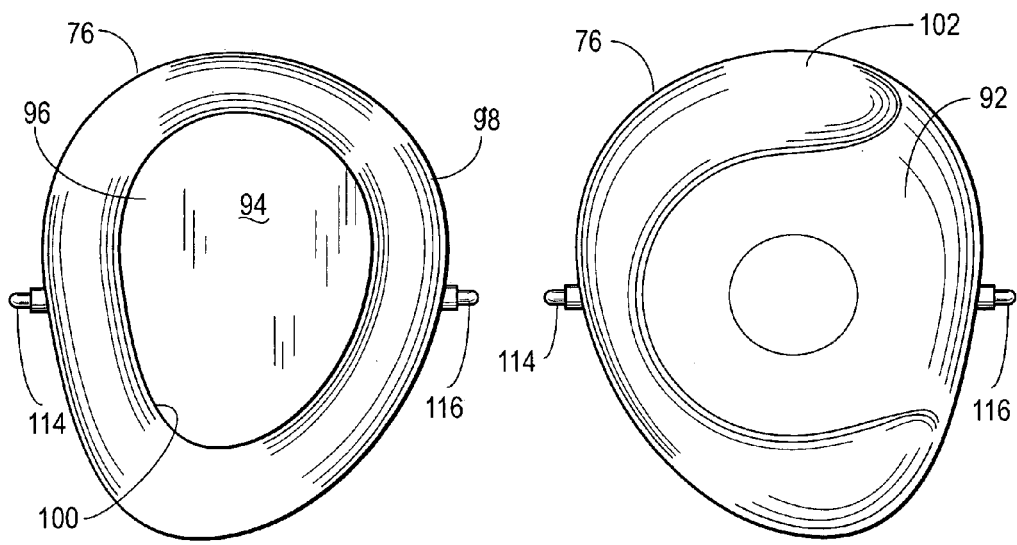
*Fig. 9*  *Fig. 10*
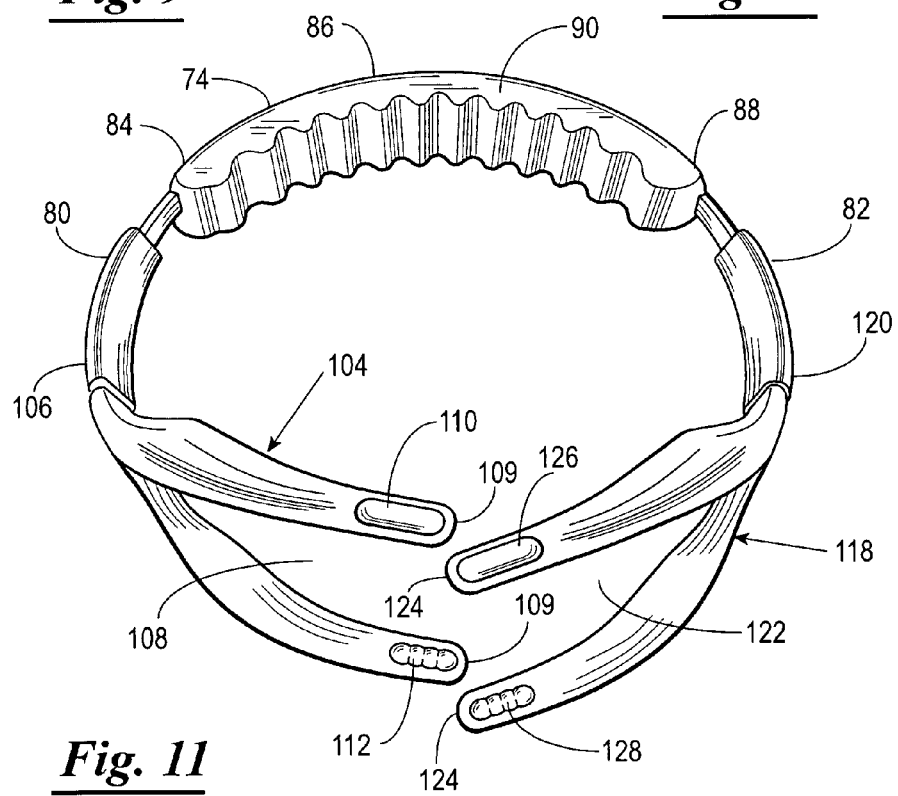
*Fig. 11* ced Faraday EARMUFF HAVING ANATOMICALLY CORRECT EAR CUPS

CROSS REFERENCE TO RELATED APPLICATIONS

This Application claims the benefit under 35 U.S.C. § 119(e) of U.S. Provisional Application No. 60/445,744, filed on Feb. 7, 2003, the entire content of which is hereby incorporated by reference.

STATEMENT REGARDING FEDERALLY SPONSORED RESEARCH OR DEVELOPMENT

Not applicable.

FIELD OF THE INVENTION

The present invention relates generally to the field of protective earmuffs for encompassing and shielding the ears of a person from harmful and annoying noise, and more particularly but not by way of limitation, to protective earmuffs having anatomically correct ear cups.

BRIEF DESCRIPTION OF THE DRAWINGS

FIG. 3 is a perspective view of the anatomically correct right-hand ear cup of the earmuff of FIG. 1 illustrating an ear receiving chamber of the anatomically correct right-hand ear cup.

FIG. 4 is a perspective view of a back side of the anatomically correct right-hand ear cup of FIG. 3 showing the connection of first end mount thereto.

FIG. 5 is an exploded view of a connector assembly of the earmuff having anatomically correct ear cups of FIG. 1 illustrating the mechanism for allowing axial and lateral rotation of the ear cups.

FIG. 9 is a perspective view of the anatomically correct right-hand ear cup of the earmuff of FIG. 8 illustrating an ear receiving chamber of the anatomically correct right-hand ear cup.

FIG. 10 is a perspective view of a back side of the anatomically correct right-hand ear cup of FIG. 9.

FIG. 11 is a perspective view of a head band of the earmuff of FIG. 8 having a first and second end mount connected thereto.

DETAILED DESCRIPTION

Figure 1:
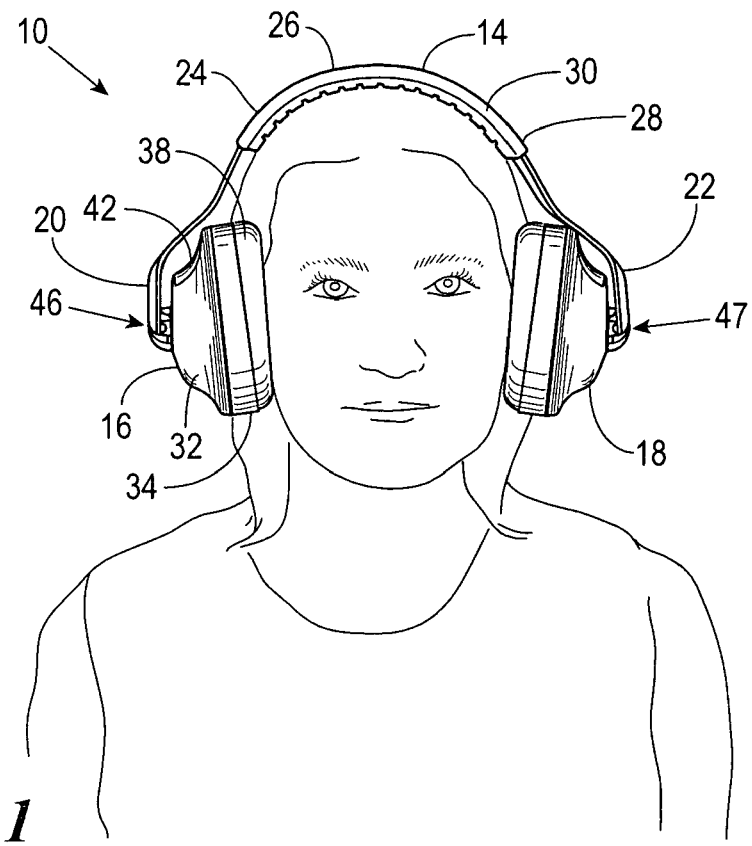
FIG. 1 is a front elevational view of an earmuff having anatomically correct ear cups constructed in accordance with the present invention, the ear cups being illustrated in a protective position over a person's ears.
Figure 2:
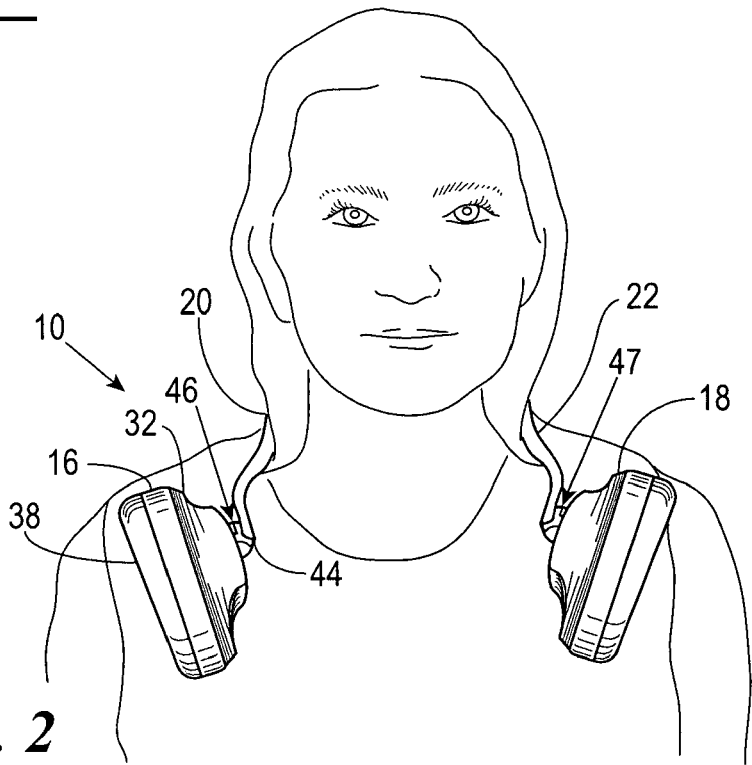
FIG. 2 is a perspective view of the earmuff having anatomically correct ear cups of FIG. 1 supported about a person's neck, the ear cups being in a non-protective position and rotated approximately 170 degrees.

Referring now to the drawings, and more particularly to FIGS. 1 and 2, shown therein is an earmuff 10 having anatomically correct ear cups constructed in accordance with the present invention. The earmuff 10 includes a head band 14, an anatomically correct right-hand ear cup 16 (also referred to herein as right-hand ear cup 16), an anatomically correct left-hand ear cup 18 (also referred to herein as left-hand ear cup 18), a first end mount 20, for connecting the right-hand ear cup 16 to the head band 14, and a second end mount 22 for connecting the left-hand ear cup 18 to the head band 14.

The term "anatomically correct ear cups" as used herein is to be understood to mean that the ear cups of the earmuff are configured to substantially cover the ears and the auditory ossicles of the person wearing the earmuff, and ear receiving chambers of the ear cups are configured to substantially correspond to the shape of the right and left ears of the person.

As shown in FIG. 1, the head band 14 is curved to generally conform to the crown of a person's head and has a right-hand end portion 24 adapted to slidably receive the first end mount 20, a medial portion 26 and a left-hand end portion 28 adapted to slidably receive the second end mount 22. A head pad 30 is connected to the medial portion 26 of the head band 14.

The interconnection of the first and second end mounts 20 and 22 to the head band 14 so as to provide adjustment of the length of the first and second end mounts 20 and 22, and thus the distance of the right-hand ear cup 16 and the left-hand ear cup from the head band 14, is well known. Thus, no further description of the interconnection of the first and second end mounts 20 and 22 to the head band 14 is believed necessary to enable one skilled in the art of protective earmuffs for encompassing and shielding ears of a person from harmful and annoying noise to understand and practice the present invention.

As will be described in more detail herein after, the interconnection of the first and second end mounts 20 and 22 to the right-hand ear cup 16 and the left-hand ear cup 18, respectively, permits the right and left-hand ear cups 16, 18 to be axially rotated so that the right and left ear cups are in proper covering alignment with the person's right and left ears as shown in FIG. 1, while also permitting the right and left ear cups 16 and 18 to be laterally moved to a comfortable, non-interfering position away from a person's body when the head band 14 is disposed in a storage position about a person's neck as shown in FIG. 2.

It should be noted that the right-hand ear cup 16 and the left-hand ear cup 18 are identical in construction and are mirror images of one another. Thus, only the right-hand ear cup 16 and its connection to the first end mount 20 will be described in detail herein after.

The right-hand ear cup 16 is provided with a back side portion 32 and a front side portion 34 having a chamber 36 formed therein (FIG. 3). The right-hand ear cup 16 is shaped such that, when the right-hand ear cup 16 is positioned over the right ear of a person, the right-hand ear cup 16 covers the right ear of the person and the auditory ossicles associated with the right ear. The right-hand ear cup 16 is further provided with a volume expansion ring 38 detachably connected to the front side portion 34 of the right-hand ear cup 16 so as to be in a covering position over the chamber 36 of the right-hand ear cup 16. The volume expansion ring 38 is provided with an opening 40 extending there through which is shaped and sized to receive the person's right ear when the right-hand ear cup 16 is disposed over the person's right ear. Since the volume expansion is detachably connected to the right-hand ear cup 16, different and/or a plurality of volume expansion rings can be employed in place of the volume expansion ring 38 for providing attenuation adjustment when required.

As more clearly shown in FIGS. 4 and 5, back side portion 32 of the right-hand ear cup 16 is provided with recessed or indented portions 42. The indented portion 42 on an upper portion of the back side portion 32 of the right-hand ear cup 16 enables the person using the earmuff 10 to wear a hard hat or other types of hats or caps without interfering with the use of the earmuff 10; and the indented portion 42 on a lower portion of the back side 32 of the right-hand ear cup 16 provides gun clearance when the person using the earmuff 10 is firing a shoulder gun for recreation and/or sport.

The back side portion 32 of the right-hand ear cup 16 is connected to a distal end portion 44 of the first end mount 20 via a first connector assembly 46 (FIG. 4) and the left-hand ear cup 18 is similarly connected to a second connector assembly 47 (FIGS. 1 and 2) which permits one to axially rotate the right-hand ear cup 16 and the left-hand ear cup 18 to ensure a proper fit of the right-hand ear cup 16 over the right ear and its associated auditory ossicles and the left-hand ear cup 18 over the left ear and its associated auditory ossicles, as well as placement of the head band 14 on the person's head, while at the same time permitting the right-hand ear cup 16 and the left-hand ear cup 18 to be laterally rotated approximately 170 degrees when the earmuff 10 is worn in a storage position around a person's neck (FIG. 2)

It should be noted that the first connector assembly 46 for connecting the right-hand ear cup 16 to the first end mount 20 and the second connector assembly 47 for connecting the left-hand ear cup 18 to the second end mount 22 are identical in construction and function. Thus, only the first connector assembly 46 for connecting the right-hand ear cup 16 to the distal end portion 44 of the first end mount 20 will be described with reference to FIGS. 5–7.

The back side portion 32 of the right-hand ear cup 16 is provided with a substantially planar connecting area 48 adapted to receive a housing or cap of the first connector assembly 46, such as substantially dome-shaped housing 50. Centrally disposed within the substantially planar connecting area 48 is a post 52 having an enlarged circular shaped head 54 on its distal end. As will be setforth in more detail herein after, the inter connection of the dome-shaped housing 50 and the post 52 permits the desired axial rotation of the right-hand ear cup 16.

Figure 6:
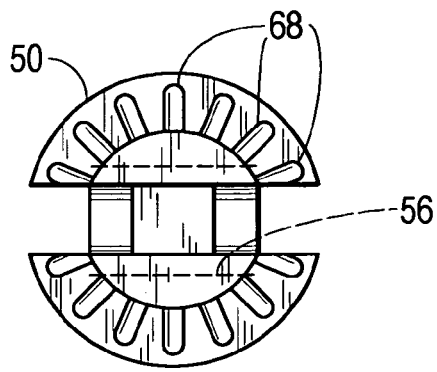
FIG. 6 is a bottom plan view of a dome-shaped housing of the connector assembly of FIG. 5.
Figure 7:
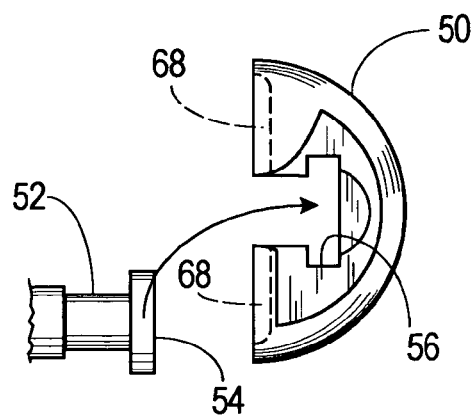
FIG. 7 is a side elevational view of the dome-shaped housing and a post of the connector assembly of FIG. 5.

As more clearly shown in FIGS. 6 and 7, the dome-shaped housing 50 is provided with a substantially T-shaped slot 56 adapted to receive the post 52 and its enlarged circular shaped head 54. Thus, upon positioning the post 52 in the T-shaped slot 56, the dome-shaped housing 50 is connected to the post 52 and the enlarged circular shaped head 54 of the post 52 permits the dome-shaped housing 50 to axially rotate about the post 52.

Referring now to FIG. 5, the distal end portion 44 of the first end mount 20 defines a yoke 58 having a substantially U-shaped opening 60. A pair of lugs 62 and 64 extend from the yoke 58 a predetermined distance into the substantially U-shaped opening 60 substantially as shown. To connect the yoke 58 to the dome-shaped housing 50, and thereby secure the dome-shaped housing 50 on the post 52, and the yoke 58 is spread open a distance sufficient to allow the lugs 62 and 64 to be aligned with the T-shaped slot 56 in the dome-shaped housing 50. Thereafter, the yoke is released and the lugs 62 and 64 are inserted into the T-shaped slot 56 thereby securing the right-hand ear cup 16 to the first end mount 20 via the dome-shaped housing 50, the post 52 and the yoke 58.

As previously stated, the inter connection of the right-hand ear cup 16 to the first end mount 20 permits the right-hand ear cup 16 to axially rotated about the post 52. To stabilize the right-hand ear cup 16 in a desired position, the back side portion 32 of the right-hand ear cup 16 is provided with a plurality of rib members 66 extending outwardly from the post 52 and terminating substantially adjacent the outer perimeter of the substantially planar connecting area 48; and the dome-shaped housing 50 is provided with a plurality of teeth 68. The teeth 68 are spaced a distance from one another so that when the dome-shaped housing 50 is connected the right-hand ear cup 16, the rib members 66 formed on the back side of the right-hand ear cup 16 are positioned between adjacent teeth 68 of the dome-shaped housing 50. Thus, once the right-hand ear cup 16 is rotatably moved to a desired position, the rib members 66 and the teeth 68 cooperate to maintain the right-hand ear cup 16 in the desired position.

As previously stated, the inter connection of the left-hand ear cup 18 to the second end mount 22 is identical to that described above with reference to the right-hand ear cup 16 and the first end mount 20. Thus, the right and left-hand ear cups 16 and 18 can be axially rotated independently of each other, and the inter connection of the first and second end mounts 20 and 22 to the right hand and left-hand cups 16 and 18 via the first and second connector assemblies 46 and 47, permit the right and left-hand cups 16 and 18 to be laterally rotated to a storage position independently of one another.

While the first connector assembly 46 has been shown as having a dome-shaped housing 50, it should be understood that the housing of the first and second connector assemblies 46 and 47 can be of any configuration as long as the inner connection of the housings to their respective end mounts permits the right-hand ear cup 16, and the left-hand ear cup 18 to be laterally rotated as described above.

Figure 8:
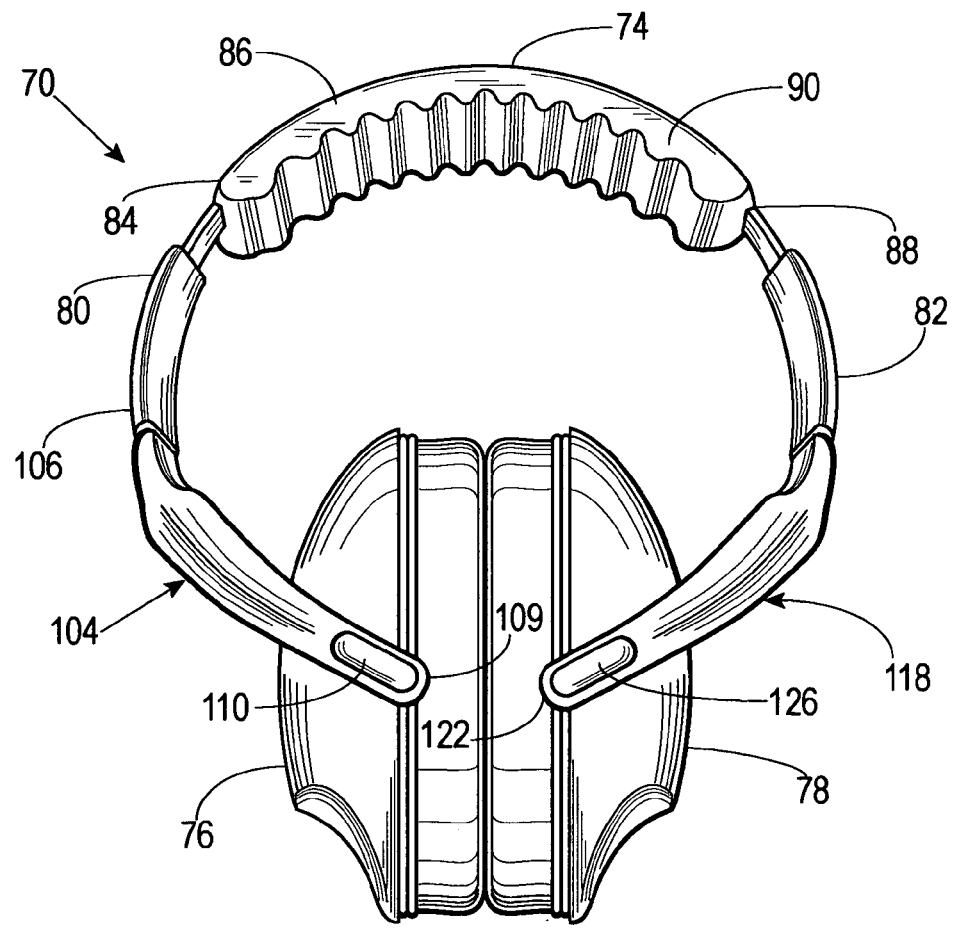
FIG. 8 is a perspective view of another embodiment of an ear muff having anatomically correct ear cups.

Referring now to FIG. 8, shown therein is another embodiment of an earmuff 70 having anatomically correct ear cups constructed in accordance with the present invention. The earmuff 70 includes a head band 74, an anatomically correct right-hand ear cup 76 (also referred to herein as right-hand ear cup 76), an anatomically correct left-hand ear cup 78 (also referred to herein as left-hand ear cup 78), a first end mount 80 for connecting the right-hand ear cup 76 to the head band 74, and a second end mount 82 for connecting the left-hand ear cup 78 to the head band 74.

The head band 74 is curved to generally conform to the crown of a person's head and has a right-hand end portion 84 adapted to slidably receive the first end mount 80, a medial portion 86 and a left-hand end portion 88 adapted to slidably receive the second end mount 82. A head pad 90 is connected to the medial portion 86 of the head band 74.

The interconnection of the first and second end mounts 80 and 82 to the head band 74 so as to provide adjustment of the length of the first and second end mounts 80 and 82, and thus the distance of the right-hand ear cup 76 and the left-hand ear cup 78 from the head band 74, is well known. Thus, no further description of the interconnection of the first and second end mounts 80 and 82 to the head band 74 is believed necessary to enable one skilled in the art of protective earmuffs for encompassing and shielding ears of a person from harmful and annoying noise to understand and practice the present invention. As will be described in more detail herein after, the interconnection of the first and second end mounts 80 and 82 to the right-hand ear cup 76 and the left-hand ear cup 78, respectively, permits alignment of the right and left-hand ear cups 76 and 78 within a distal end portion of the first and second end mounts 80 and 82.

It should be noted that the right-hand ear cup 76 and the left-hand ear cup 78, and the first and second end mount 80 and 82 are identical in construction and are mirror images of one another. Thus, only the right-hand ear cup 76 and its connection to the first end mount 80 will be described in detail herein after.

The right-hand ear cup 76 is provided with a back side portion 92 (FIG. 10) and a front side portion 94 having a chamber 96 formed therein (FIG. 9). The right-hand ear cup 76 is shaped such that, when the right-hand ear cup 76 is positioned over the right ear of a person, the right-hand ear cup 76 covers the right ear of the person and the auditory ossicles associated with the right ear. The right-hand ear cup 76 is further provided with a volume expansion ring 98 detachably connected to the front side portion 94 of the right-hand ear cup 76 so as to be in a covering position over the chamber 96 of the right-hand ear cup 76. The volume expansion ring 98 is provided with an opening 100 extending there through which is shaped and sized to receive the person's a right ear when the right-hand ear cup 76 is disposed over the person's right ear. Since the volume expansion ring 98 is detachably connected to the right-hand ear cup 76, different and/or a plurality of volume expansion rings can be employed in place of the volume expansion ring 98 for providing attenuation adjustment when required.

The back side portion 92 of the right-hand ear cup 76 is provided with recessed or indented portions 102. The indented portion 102 on an upper portion of the back side portion 92 of the right-hand ear cup 76 enables the person using the earmuff 70 to wear a hard hat or other types of hats or caps without interfering with the use of the earmuff 70; and the indented portion 102 on a lower portion of the back side portion 92 of the right-hand ear cup 76 provides gun clearance when the person using the earmuff 70 is firing a shoulder gun for recreation and/or sport.

Figure 12:
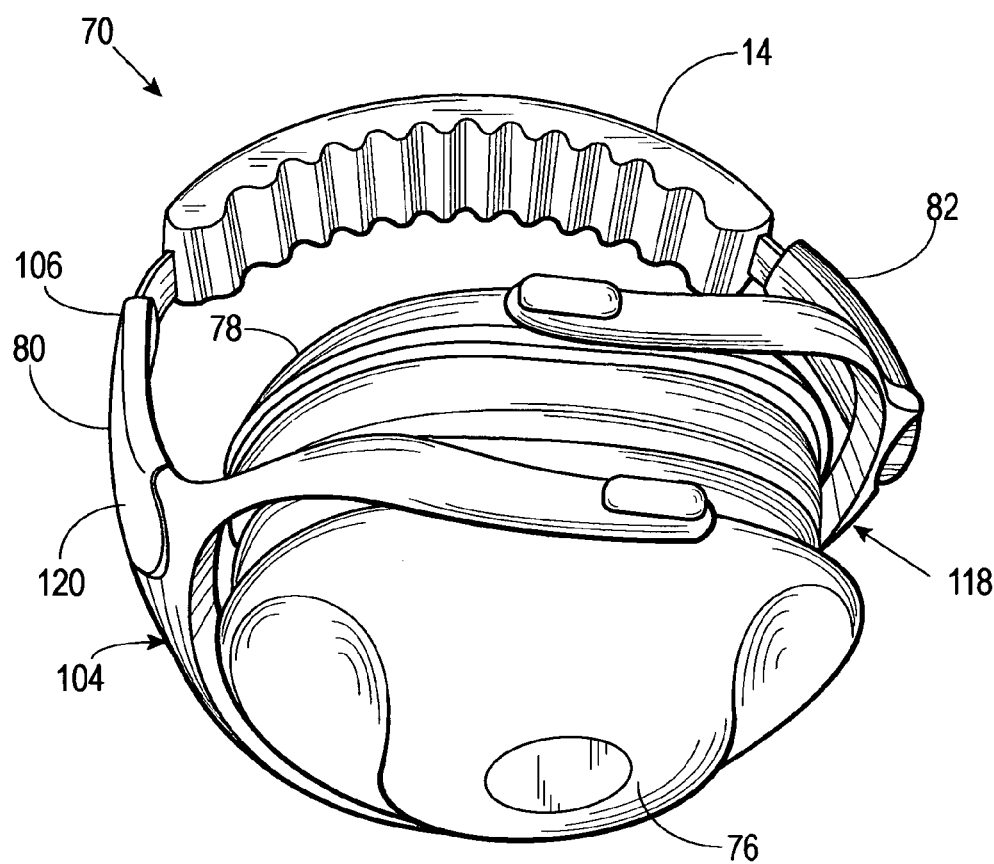
FIG. 12 is a perspective view of the earmuff of FIG. 8 in a folded, storage position.

Shown in FIG. 11, a yoke 104 is pivotally connected to a distal end 106 of the first end mount 80, and the yoke 104 defines an opening 108 adapted to receive the right-hand ear cup 76. Disposed near a distal end 109 of the yoke 104 are housings 110 containing a plurality of step portions 112 adapted to pivotally receive pivot pins 114 and 116 disposed on opposite sides of the right-hand ear cup 76 substantially as shown. Similar, a yoke 118 is pivotally connected to a distal end 120 of the second end mount 82, and the yoke 118 defines an opening 122 adapted to receive the left-hand ear cup 78. Disposed near a distal end 124 of the yoke 118 are housings 126 containing a plurality of step portions 128 adapted to pivotally receive pivot pins (not shown) of the left-hand ear cup 78. Thus, the right-hand ear cup 76 can be aligned within the opening 100 in the yoke 104 and the left-hand ear cup 78 can be aligned within the opening 122 in the yoke 118, since the first and second end mounts 80 and 82 can be adjusted length wise in a conventional manner such that the right-hand ear cup 76 and the left-hand ear cup 78 are secured in a proper fitting position. The pivotal connection of the distal end 106 of the first end mount 80 to yoke 104, in combination with the pivotal connection of the right-hand ear cup 76 to the yoke 104, and the pivotal connection of the distal end 120 of the second end mount 82 to the yoke 118, in combination with the pivotal connection of the left-hand ear cup 78 to the yoke 118 permits the ear muff 70 to be stored in a folded position substantially as shown in FIG. 12.

The ear muffs 10 and 70 herein described are desirably fabricated of a combination or plastic materials, rubber and metal. In addition, it is clear from the above description that the present invention is well adapted to carry out the objects and to obtain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and claimed.

What is claimed is:

1. An earmuff having anatomically correct ear cups, comprising:
   a head band having a right end portion, a medial portion and a left end portion, the head band curved to generally conform to a crown of a person's head;
   a first end mount connected to the right end portion of the head band such that the first end mount is adjustable relative to the head band, a distal end portion of the first end mount defining a yoke;
   a second end mount connected to the left end portion of the head band such that the second end mount is adjustable relative to the head band, a distal end of the second end mount defining a yoke;
   a right ear cup;
   a left ear cup;
   a first connector assembly for connecting the right ear cup to the yoke of the first end mount such that the right ear cup is axially rotatable for providing proper covering alignment with the person's right ear when the earmuff is disposed on the person in an operative, protective position, while permitting the right ear cup to be laterally moved to a position away from the person's body when the head band of the ear muff is disposed in a storage position about the person's neck; and
   a second connector assembly for connecting the left ear cup to the yoke of the second end mount such that the left ear cup is axially rotatable for providing proper covering alignment with the person's left ear when the earmuff is disposed on the person in an operative, protective position, while permitting lateral movement of the left ear cup away from the person's body when the head band of the earmuff is disposed in a storage position about the person's neck,
   wherein the right ear cup and the left ear cup are each provided with a back side portion and a front side portion, the front side portion of each of the right ear cup and the left ear cup having a chamber formed therein, and wherein the yoke defined by the distal end portion of the first end mount comprising a pair of oppositely disposed, aligned lugs extending inwardly a distance into an opening of the yoke, the opening in the yoke sized and configured to receive at least a portion of the first connector assembly for connecting the right ear cup to the yoke of the first end mount, and the yoke defined by the distal end portion of the second end mount comprising a pair of oppositely disposed, aligned lugs extending inwardly a distance into an opening of the yoke, the opening in the yoke sized and configured to receive at least a portion of the second connector assembly for connecting the left ear cup to the yoke of the second end mount and wherein the first connector assembly comprises:
   a right ear cup connector disposed on the back side portion of the right ear cup; and a first end mount connector pivotally connected to the yoke defined in the distal end portion of the first end mount such that, upon connecting the right ear cup connector to the first end mount connector, the right ear cup is axially and laterally rotatable relative to the first end mount;

and wherein the second connector assembly comprises:

a left ear cup connector disposed on the back side portion of the left ear cup; and a second end mount connector pivotally connected to the yoke defined in the distal end portion of the second end mount such that, upon connecting the left ear cup connector to the second end mount connector, the left ear cup is axially and laterally rotatable relative to the second end mount.

2. The earmuff having anatomically correct ear cups of claim 1 further comprising:

a right volume expansion ring connectable to the right ear cup; and a left volume expansion ring connectable to the left ear cup.

3. The earmuff having anatomically correct ear cups of claim 1 wherein the right ear cup connector comprises:

a post disposed on the backside portion of the right ear cup and extending outwardly therefrom; and an enlarged head disposed on a distal end of the post;

and wherein the first end mount connector comprises:

a housing having a substantially T-shaped slot extending therethrough for receiving the enlarged head of the right ear cup connector, the housing further provided with aligned, oppositely disposed cutaway portions on an upper portion thereof such that the cutaway portions are disposed above opposite ends of the substantially T-shaped slot;

and wherein the left ear cup connector comprises:

a post disposed on the backside portion of the left ear cup and extending outwardly therefrom; and an enlarged head disposed on a distal end of the post;

and wherein the second end mount connector comprises;

a housing having a substantially T-shaped slot extending therethrough for receiving the enlarged head of the left ear cup connector, the housing further provided with aligned, oppositely disposed cutaway portions on an upper portion thereof such that the cutaway portions are disposed above opposite ends of the substantially T-shaped slot.

4. The earmuff having anatomically correct ear cups of claim 3 wherein the first connecter assembly further comprising;

a plurality of spatially disposed rib members formed on the backside of the right ear cup so as to extend outwardly from the post; and a plurality of spatially disposed teeth formed in at least a portion of a lower surface of the housing, the spatially disposed rib members and the spatially disposed teeth cooperating to permit axial rotation of the right ear cup about the post of the first connector assembly while stabilizing the right ear cup in a desired position due to meshing of the rib members with the teeth;

and wherein the second connector assembly further comprises:

a plurality of spatially disposed rib members formed on the backside of the left ear cup so as to extend outwardly from the post; and a plurality of spatially disposed teeth formed in at least a portion of a lower surface of the housing, the spatially disposed rib members and the spatially disposed teeth cooperating to permit axial rotation of the left ear cup about the post of the second connector means while stabilizing the left ear cup in a desired position due to meshing of the rib members with the teeth.

5. The earmuff having anatomically correct ear cups of claim 1 wherein the backside portion of each of the right ear cup and the left ear cup is provided an upper indented portion and a lower indented portion, the upper indented portion facilitating the wearing of a hard hat and the lower indented portion facilitating the firing of a shoulder gun for recreation and sport.

6. An earmuff having anatomically correct ear cups, comprising:

a head band having a right end portion, a medial portion and a left end portion, the head band curved to generally conform to a crown of a person's head;

a first end mount connected to the right end portion of the head band such that the first end mount is adjustable relative to the head band, a distal end portion of the first end mount defining a yoke;

a second end mount connected to the left end portion of the head band such that the second end mount is adjustable relative to the head band, a distal end of the second end mount defining a yoke;

a right ear cup;

a left ear cup;

a first connector assembly for connecting the right ear cup to the yoke of the first end mount such that the right ear cup is axially rotatable for providing proper covering alignment with the person's right ear when the earmuff is disposed on the person in an operative, protective position, while permitting the right ear cup to be laterally moved to a position away from the person's body when the head band of the ear muff is disposed in a storage position about the person's neck; and a second connector assembly for connecting the left ear cup to the yoke of the second end mount such that the left ear cup is axially rotatable for providing proper covering alignment with the person's left ear when the earmuff is disposed on the person in an operative, protective position, while permitting lateral movement of the left ear cup away from the person's body when the head band of the earmuff is disposed in a storage position about the person's neck, wherein the right ear cup and the left ear cup are each provided with a back side portion and a front side portion, the front side portion of each of the right ear cup and the left ear cup having a chamber formed therein and the back side portions thereof having a substantially planar connecting area provided thereon, and wherein the yoke defined by the distal end portion of the first end mount comprising a pair of oppositely disposed, aligned lugs extending inwardly a distance into an opening of the yoke, the opening in the yoke sized and configured to receive at least a portion of the first connector assembly for connecting the right ear cup to the yoke of the first end mount, and the yoke defined by the distal end portion of the second end mount comprising a pair of oppositely disposed, aligned lugs extending inwardly a distance into an opening of the yoke, the opening in the yoke sized and configured to receive at least a portion of the second connector assembly for connecting the left ear cup to the yoke of the second end mount and wherein the first connector assembly comprises:

a right ear cup connector disposed on the substantially planar connecting area of the back side portion of the right ear cup; and a first end mount connector pivotally connected to the yoke defined in the distal end portion of the first end mount via the oppositely disposed lugs of the yoke of the first end mount;

and wherein the second connector assembly comprises:

a left ear cup connector disposed on the substantially planar area on the back side portion of the left ear cup; and a second end mount connector pivotally connected to the yoke defined in the distal end portion of the second end mount via the oppositely disposed lugs of the yoke of the second end mount.

7. The earmuff having anatomically correct ear cups of claim 6 wherein the right ear cup connector comprises:

a post substantially centrally disposed in the substantially planar connecting area on the backside portion of the right ear cup; and an enlarged circular head disposed on a distal end of the post;

and wherein the first end mount connector comprises:

a housing having a substantially T-shaped slot extending therethrough for receiving the enlarged circular head of the right ear cup connector, the housing further provided with aligned, oppositely disposed cutaway portions on an upper portion thereof such that the cutaway portions are disposed above opposite ends of the substantially T-shaped slot;

and wherein the left ear cup connector comprises:

a post disposed on the backside portion of the left ear cup and extending outwardly therefrom; and an enlarged circular head disposed on a distal end of the post;

and wherein the second end mount connector comprises;

a housing having a substantially T-shaped slot extending therethrough for receiving the enlarged circular head of the left ear cup connector, the housing further provided with aligned, oppositely disposed cutaway portions on an upper portion thereof such that the cutaway portions are disposed above opposite ends of the substantially T-shaped slot.

8. The earmuff having anatomically correct ear cups of claim 7 wherein the first connecter assembly further comprises:

a plurality of spatially disposed rib members formed on the backside of the right ear cup so as to extend outwardly from the post and terminating substantially adjacent a perimeter of the substantially planar connecting area; and a plurality of spatially disposed teeth formed in at least a portion of a lower surface of the housing, and the spatially disposed rib members and the spatially disposed teeth cooperating to permit axial rotation of the right ear cup about the post of the first connector assembly while stabilizing the right ear cup in a desired position due to meshing of the rib members with the teeth;

and wherein the second connector assembly further comprises:

a plurality of spatially disposed rib members formed on the backside of the right ear cup so as to extend outwardly from the post and terminating substantially adjacent a perimeter of the substantially planar connecting area; and a plurality of spatially disposed teeth formed in at least a portion of a lower surface of the housing, the spatially disposed rib members and the spatially disposed teeth cooperating to permit axial rotation of the right ear cup about the post of the first connector assembly while stabilizing the right ear cup in a desired position due to meshing of the rib members with the teeth.

9. The earmuff having anatomically correct ear cups of claim 8 wherein the backside portion of each of the right ear cup and the left ear cup is provided an upper indented portion and a lower indented portion, the upper indented portion facilitating the wearing of a hard hat and the lower indented portion facilitating the firing of a shoulder gun for recreation and sport.

10. An earmuff having anatomically correct ear cups, comprising:

a head band having a right end portion, a medial portion and a left end portion, the head band curved to generally conform to a crown of a person's head;

a first end mount connected to the right end portion of the head band such that the first end mount is adjustable relative to the head band, a distal end portion of the first end mount defining a yoke;

a second end mount connected to the left end portion of the head band such that the second end mount is adjustable relative to the head band, a distal end of the second end mount defining a yoke;

an anatomically correct right ear cup defining a chamber having an opening shaped to substantially correspond to the shape of a person's right ear;

an anatomically correct left ear cup defining a chamber having an opening shaped to substantially correspond to the shape of a person's left ear;

first connecting means for connecting the anatomically correct right ear cup to the yoke of the first end mount such that the anatomically correct right ear cup is axially rotatable for providing proper covering alignment with the person's right ear when the earmuff is disposed on the person in an operative, protective position, while permitting the anatomically correct right ear cup to be laterally moved to a position away from the person's body when the head band of the ear muff is disposed in a storage position about the person's neck; and second connecting means for connecting the anatomically correct left ear cup to the yoke of the second end mount such that the anatomically correct left ear cup is axially rotatable for providing proper covering alignment with the person's left ear when the earmuff is disposed on the person in an operative, protective position, while permitting lateral movement of the anatomically correct left ear cup away from the person's body when the head band of the earmuff is disposed in a storage position about the person's neck, wherein the anatomically correct right ear cup and the anatomically correct left ear cup are each provided with a back side portion and a front side portion, the front side portion of each of the anatomically correct right ear cup and the anatomically correct left ear cup having the chamber formed therein and the back side portions thereof having a connecting area formed thereon, the yoke defined by the distal end portion comprising a pair of oppositely disposed, aligned lugs extending inwardly a distance into an opening of the yoke, the opening in the yoke sized and configured to receive at least a portion of the right ear cup, and wherein the first connecting means connecting the right ear cup to the yoke of the first end mount comprises:

a post substantially centrally disposed in the connecting area formed on the back side portion of the anatomically correct right ear cup and extending outwardly therefrom, the post having a circular shaped head on a distal end thereof;

a substantially dome-shaped housing having a substantially T-shaped slot in a lower portion thereof, the substantially T-shaped slot adapted to slidably receive the post such that the circular shaped head on the distal end of the post is retained in the substantially T-shaped slot, the substantially dome-shaped housing further having aligned, oppositely disposed cutaway portions on an upper portion thereof, the cutaway portions being disposed above opposite ends of the substantially T-shaped slot such that, upon connecting the substantially dome-shaped housing to the yoke of the first end mount, the lugs of the yoke extend inwardly into the substantially T-shaped slot and secure the anatomically correct right ear cup to the yoke of the first end mount and thereby provide axial and lateral rotation of the anatomically correct right ear cup;

and wherein the second connecting means for connecting the anatomically correct left ear cup to the yoke of the second end mount comprises:

a post substantially centrally disposed in the connecting area formed on the back side portion of the anatomically correct left ear cup and extending outwardly therefrom, the post having a circular shaped head on a distal end thereof;

a substantially dome-shaped housing having a substantially T-shaped slot in a lower portion thereof, the substantially T-shaped slot adapted to slidably receive the post such that the circular shaped head on the distal end of the post is retained in the substantially T-shaped slot, the substantially dome-shaped housing further having aligned, oppositely disposed cutaway portions on an upper portion thereof, the cutaway portions being disposed above opposite ends of the substantially T-shaped slot such that, upon connecting the substantially dome-shaped housing to the yoke of the second end mount, the lugs of the yoke extend inwardly into the substantially T-shaped slot and thereby secures the anatomically correct left ear cup to the yoke of the second end mount and thereby provide axial and lateral rotation of the anatomically correct left ear cup.

11. The earmuff having anatomically correct ear cups of claim 10 further comprising:

a right volume expansion ring having an outer periphery and an inner periphery, a portion of the outer periphery of the right volume expansion ring substantially corresponding in size and shape to a periphery of the anatomically correct right ear cup, the inner periphery of the right volume expansion ring shaped to substantially correspond to the shape of the right ear of the person and sized to permit communication of the right ear with the chamber of the anatomically correct right ear cup when the right volume expansion ring is connected to the anatomically correct right ear cup; and a left volume expansion ring connectable to the anatomically correct left ear cup, the left volume expansion ring having an outer periphery and an inner periphery, a portion of the outer periphery of the left volume expansion ring substantially corresponding in size and shape to a periphery of the anatomically correct left ear cup, the inner periphery shaped to substantially correspond to the shape of the left ear of the person and sized to permit communication of the left ear with the chamber of the anatomically correct left ear cup when the left volume expansion ring is connected to the anatomically correct left ear cup.

12. The earmuff having anatomically correct ear cups of claim 10 wherein the first connector means for connecting the anatomically correct right ear cup to the yoke of the first end mount further comprises:

a plurality of spatially disposed rib members extending outwardly from the post and terminating substantially adjacent an outer perimeter of the connecting area formed on the back side portion of the anatomically correct right ear cup; and a plurality of spatially disposed teeth formed in a lower surface of the substantially dome-shaped housing, the spatially disposed rib members and the spatially disposed teeth cooperating to permit axial rotation of the anatomically correct right ear cup about the post of the first connector means while stabilizing the anatomically correct right ear cup in a desired position due to meshing of the rib members with the teeth;

and wherein the second connector means for connecting the anatomically correct left ear cup to the yoke of the second end mount further comprises:

a plurality of spatially disposed rib members extending outwardly from the post and terminating substantially adjacent an outer perimeter of the connecting area formed on the back side portion of the anatomically correct left ear cup; and a plurality of spatially disposed teeth formed in a lower surface of the substantially dome-shaped housing, the spatially disposed rib members and the spatially disposed teeth cooperating to permit axial rotation of the anatomically correct left ear cup about the post of the second connector means while stabilizing the anatomically correct left ear cup in a desired position due to meshing of the rib members with the teeth.

13. The earmuff having anatomically correct ear cups of claim 12 wherein the back side portion of each of the anatomically correct right ear cup and the anatomically correct left ear cup is provided with an upper indented portion and a lower indented portion, the upper indented portion facilitating the wearing of a hard hat and the lower indented portion facilitating the firing of a shoulder gun for recreation and sport.

\* \* \* \* \*